Figure 1:
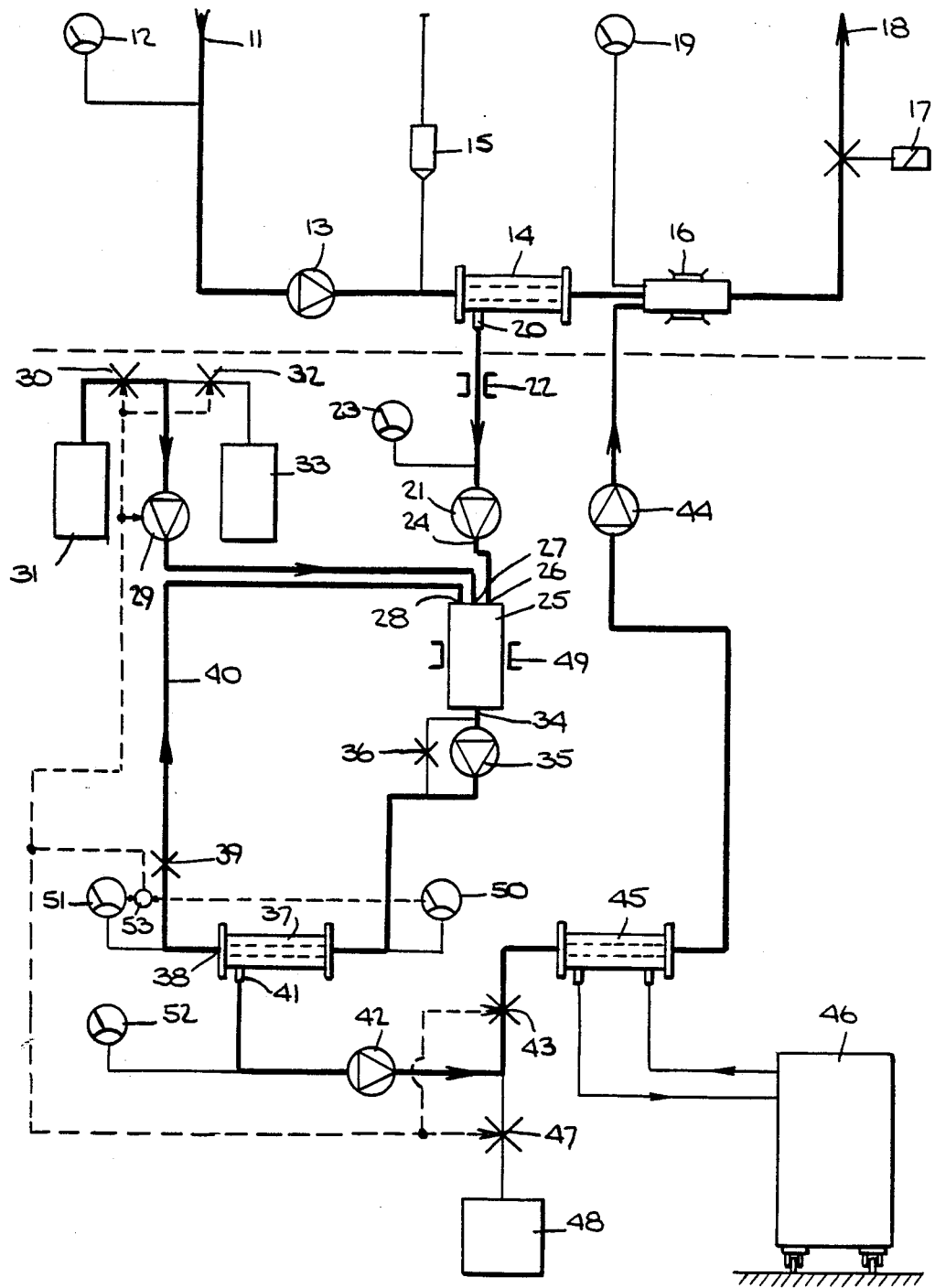

United States Patent [19]
Seidel et al.

[11] Patent Number: 4,923,439
[45] Date of Patent: May 8, 1990

[54] PROCESS FOR THE SELECTIVE EXTRACORPOREAL PRECIPITATION OF LOW-DENSITY LIPOPROTEINS FROM WHOLE SERUM OR PLASMA

[75] Inventors: Dietrich Seidel, Göttingen; Heinrich Wieland, Waake; Gerhard Rosskopf, Fuldabrück-Dörnhagen; Dieter Rath, Melsungen, all of Fed. Rep. of Germany

[73] Assignee: B. Braun-SSC AG, Emmenbrucke, Switzerland

[21] Appl. No.: 172,953

[22] Filed: Mar. 23, 1988

Related U.S. Application Data

[63] Continuation of Ser. No. 769,761, Aug. 26, 1985, abandoned, which is a continuation of Ser. No. 414,809, Sep. 3, 1982, abandoned.

[30] Foreign Application Priority Data

Sep. 10, 1981 [DE] Fed. Rep. of Germany ....... 3135814
May 13, 1982 [DE] Fed. Rep. of Germany ....... 3217925

[51] Int. Cl.$^5$ ............................................. G01N 33/48
[52] U.S. Cl. ......................................... 604/6; 436/13; 436/71; 436/86; 604/5
[58] Field of Search ................. 436/13, 71, 86; 604/5, 604/6; 260/112 R

[56] References Cited

U.S. PATENT DOCUMENTS

| | | | |
|---|---|---|---|
| 3,955,925 | 5/1976 | Proksch et al. | 436/13 |
| 4,103,685 | 8/1978 | Lupien et al. | 422/44 X |
| 4,110,077 | 8/1978 | Klein et al. | 436/71 X |
| 4,215,993 | 8/1980 | Sanders | 436/86 X |
| 4,264,471 | 4/1981 | Briggs | 436/13 X |

*Primary Examiner*—Michael S. Marcus
*Attorney, Agent, or Firm*—Kenyon & Kenyon

[57] ABSTRACT

Processes are described for the selective extracorporeal precipitation of low density lipoproteins or beta-lipoproteins from whole serum or plasma, wherein a treating agent comprising heparin or a polyanion, such as dextran sulfate or sodium-phosphorus tungstate, in a buffer is added to the whole serum or plasma and the beta-llipoprotein-complex which thereupon forms with the treating agent is precipitated at the isoelectric point at a pH value in the range of from about 5.05 to about 5.25, and is then separated. Optionally, the precipitate or respecively the filtrate is further analyzed for diagnostic purposes. When heparin is employed, the process may be employed therapeutically.

Apparatus is described for the continuous therapeutic practice of such a process, employing heparin, including means for flushing to reduce clogging of the filter employed to separate the precipitated lipoprotein-complex.

18 Claims, 2 Drawing Sheets

PROCESS FOR THE SELECTIVE EXTRACORPOREAL PRECIPITATION OF LOW-DENSITY LIPOPROTEINS FROM WHOLE SERUM OR PLASMA

This is a continuation of application Ser. No. 06/769,761, filed Aug. 26, 1985, now abandoned, which is a continuation of application Ser. No. 06/414,809, filed Sept. 3, 1982, abandoned.

This invention relates to processes for the extracorporeal precipitation and removal of low density lipoproteins from blood plasma or whole blood serum, and to apparatus for conducting such processes during dialysis.

BACKGROUND

The advances in recent years in the field of lipoprotein system analysis have shown that the narrow correlations found in older epidemiological data between plasma cholesterol concentrations and the risk of early atherosclerosis, especially coronary sclerosis, derive essentially from high-cholesterol beta-lipoproteins. In human blood, about 70-80% of the total cholesterol is normally found attached to the low density or beta-lipoproteins, with the remainder being distributed in other lipoprotein fractions, essentially Very Low Density Lipoproteins, High Density Lipoproteins and chylomicrons. (As employed herein, VLDL means Very Low Density Lipoproteins; LDL means Low Density Lipoproteins; and HDL means High Density Lipoproteins.) In pathological processes accompanied by a disturbed fat metabolism or increased plasmalipid concentrations and leading to early atherosclerosis, the percentage of beta-lipoprotein or beta-cholesterol in the total cholesterol may even increase further. This means that hypercholesterolemia is caused, as a rule, by hyper-beta-lipoproteinemia. In the past, therefore, many attempts have been made (1) to measure the low density lipoproteins selectively, and (2) to eliminate them from the circulating blood, selectively if possible.

Neither objective has been achieved satisfactorily until now, taking into consideration the state of the art. The usual methods of quantifying low density lipoproteins are based either on the use of the division of the lipoprotein spectrum into density classes with the aid of an ultracentrifuge, or on the division of the lipoprotein spectrum in the electric field, a method utilized in lipoprotein electrophoresis. Also there are precipitation processes which are based on the fact that apo-B-containing lipoproteins (VLDL and LDL) can be separately determined by polyanions and divalent cations from non-apo-B-containing lipoproteins by precipitation of the former. Apo-B-protein is the main protein component of the low density or beta-lipoproteins as well as of the VLDL or pre-beta-lipoproteins and chylomicrons.

The precipitation techniques have hitherto not been suitable for separating VLDL from LDL. The two first-named methods (i.e., ultracentrifugation, for which, see R. J. Havel, H. A. Eder and J. H. Bragdon: The Distribution and Chemical Composition of Ultracentrifugally Separated Lipoproteins in Human Serum, J. Clin. Invest., 34, 1345 (1955); and electrophoresis, for which, see H. Wieland and D. Seidel: Fortschritte in der Analytik des Lipoproteinmusters-Advances in analyzing the lipoprotein sample, Inn. Med., 5, 290-300 (1978)) have the disadvantage in relatively large routine series that they were either too expensive and time-consuming or could not be automated. In addition, direct measurement of the low density cholesterol was possible only after isolation of the fractions, usually with the use of an ultracentrifuge. The mathematical determination of the low density cholesterol component by electrophoresis presupposes certain premises of the protein lipid composition. The same applies to the methods which utilize precipitation techniques. The conventional precipitation techniques also have the disadvantage that they divide the lipoprotein spectrum into only two main fractions (apo-B-containing and non-apo-B-containing), that is, a distinction between or separation of VLDL and LDL is not possible.

Therapeutic efforts of effectively reducing the low density lipoproteins have thus far all been unsatisfactory. Control of the low density lipoprotein concentration by medication is extremely difficult and as a rule unsatisfactory, especially in the genetic forms of fat metabolism disorders. In the results obtained heretofore by medication, the therapeutic success of lowering the atherosclerosis risk could not be proven with certainty. Surgery, based essentially on the application of abnormal circulatory conditions or on displacement of major portions of intestine, have indeed given clear therapeutic results but cannot be regarded as generally acceptable because of the anticipated strong side effects. Such drastic therapeutic manipulations have shown, however, that with a sufficient reduction of the low density lipoproteins, not only can atherosclerotic processes be stopped, but existing atherosclerotic vessel alterations are reversible.

"Mechanical" elimination of low density lipoproteins from the blood has been tried heretofore essentially in two ways. One involves treatment of the affected patients by a so-called plasmapheresis, a method involving complete exchange of the entire blood serum. While this method has had the result of lowering the low density lipoprotein content of the affected patients, at the same time those lipoproteins which counteract atherosclerosis (high density lipoproteins) are also eliminated from the blood, on balance an undesirable therapeutic effect. Moreover, in the plasma exchange all other proteins of the plasma, including coagulation factors, globulins and hormones, are eliminated as well. Yet this method has proved quite useful for certain cases of hyper-beta-lipoproteinemia, although the search for a selective elimination of the low density lipoproteins from the plasma continues to have a high priority.

A second method of eliminating low density lipoproteins from the blood was undertaken with the aid of specific antibodies which were coupled to a matrix. The antibodies were obtained by immunization of sheep or rabbits. Although a drastic lowering of all apo-B-containing lipoproteins was achieved by such method (see A. Habenicht, Inaugural Dissertation, 1978, Heidelberg, School of Med.; W. Stoffel and Th. Demant, Selective Removal of Apolipoprotein B-containing Serum Lipoproteins from Blood Plasma, Proc. Nat. Acad. Sci. U.S.A., 78, 611-615 (1981)), the method has the disadvantage that during therapeutic application the antibodies produced in an animal inevitably get into the circulation of the treated patient, albeit in small quantities. In the long run this is bound to cause immunological problems in the person to be treated. This considerable objection to such method is the more serious because the treatment of fat metabolism disorders must be lifelong if it is to be effective and enduring. It must be noted that, especially in hereditary disorders, the therapy must begin at a youthful age in order to stop or to retard substantially the process of premature atherosclerotic vascular disease. Another disadvantage of the use of immobilized antibodies to Apo-B is that of unspecific elimination of all apo-B-containing lipoproteins. This method, therefore, is not apt to selectively eliminate low density lipoproteins as the only atherogenic lipoproteins. A major disadvantage of the simultaneous removal of VLDL is the resulting stimulation of triglyceride and cholesterol synthesis in the liver.

A third method of removing low density lipoproteins from the blood is based on the selective absorption of beta- and pre-beta-lipoproteins from whole blood by sulfated polysaccharides coupled to agarose beads, e.g., heparin or dextran according to U.S. Pat. No. 4,103,685. A disadvantage evident from the description in the patent is the low capacity of this method for eliminating the lipoproteins, as well as the fact that not only low density but also very low density lipoproteins are removed. Cholesterol reductions are described according to the method of U.S. Pat. No. 4,103,685 only for in vitro tests. As is evident from the accompanying reduction of the phospholipids and triglycerides, the cholesterol reduction appears to have been caused by a dilution of the patient's blood rather than by selective elimination.

The procedure described in U.S. Pat. No. 4,215,993, of precipitating lipoproteins generally at their isoelectric point, relates, in contrast to the method of the present invention, to the use of sodium-phosphorus tungstate. This polyanion is unphysiological and therefore, in contrast to the present process, unsuitable for use as a therapeutic treating agent. Moreover, when employing phosphorus tungstate it is not possible to eliminate or to determine low density lipoproteins selectively, so that the main objective of the present invention is not achieved. That this is so was indicated in U.S. Pat. No. 4,215,993 by, among other things, the recommendation to calculate the low density lipoproteins according to a mathematical formula (Friedewald formula) from the so-called HDL cholesterol, taking into consideration also the total cholesterol and the triglycerides. Essentially the isoelectric point precipitation using phosphorus tungstic acid, as described in such patent, does not differ in its result from the usual polyanion precipitation using bivalent cations. A complete precipitation of VLDL and LDL in such process is achieved only when polymers, such as polyvinyl pyrolidone or polyethylene glycol, of exactly defined molecular weight are added to the precipitation solution. That this cannot be achieved in an extracorporeal system is beyond question.

It should also be pointed out that U.S. Pat. No. 4,215,993 misleadingly refers to the totality of beta-lipoproteins, pre-beta-lipoproteins and chylomicrons as low density lipoproteins. Since it is a declared object of the process described in such patent to determine high density lipoproteins in the serum, it is important that the VLDL, chylomicrons and LDL occurring along with high density lipoproteins be eliminated by this precipitation method. A specific precipitation of the real low density lipoproteins or beta-lipoproteins was neither intended nor achieved.

We have now discovered processes whereby low density lipoproteins or beta-lipoproteins can be removed selectively and at a high degree of completeness from blood, i.e., from whole serum or from blood components such as plasma. When heparin is employed, such process may be employed for therapeutic purposes as well as for diagnostic purposes. We have also invented apparatus for practicing the process for therapeutic purposes.

THE PROCESS

The process for the selective extracorporeal precipitation of low density lipoprotein or beta-lipoprotein from whole serum or plasma comprises mixing whole serum or blood plasma and a composition comprising heparin in an aqueous buffer solution, whereby a complex of beta-lipoproteins and heparin is precipitated at the isoelectric point at a pH in the range of from about 5.05 to about 5.25, and typically thereafter said complex is separated from the remaining supernatant fluid.

The process is based on the absolutely specific precipitation of the beta-lipoproteins after cross-linkage with heparin by precipitation at the isoelectric point of the complex at a pH value of 5.05 to 5.25, in particular at a pH value of 5.13. Besides being specific, this process has the further advantage that the only substance which is employed for precipitating the low-density lipoproteins is heparin, a substance naturally produced in the body itself. Precipitation at the isoelectric point by lowering of the pH with the use of buffers can easily be corrected for physiological conditions by suitable filtration and pH adjustment after the isoelectric point precipitation. In particular, the complex of heparin and beta-lipoproteins is precipitated in the method of the invention at a pH value of 5.13.

The heparin is dissolved in a buffer and mixed with the whole serum or plasma. The buffer serves to adjust and stabilize the stated pH values. All buffer mixtures which in the stated pH range ensure stability are in principle usable in practicing the process. Buffers most suitable for therapeutic purposes are a phosphate buffer, a citrate buffer, a phosphate-citrate buffer, a lactate buffer or an acetate buffer, or mixtures thereof.

When employed for therapeutic purposes, the ratio of buffer to serum or plasma or blood volume may be between 1:5 and 5:1 by volume. A most favorable ratio was found to be 1:1. When employed for the selective elimination of low density lipoproteins for diagnostic purposes, the ratio of buffer to serum, plasma or blood may be in the range of from about 2:1 to about 10:1 by volume.

The heparin concentration is not a particularly critical variable. It is desirable to employ heparin concentrations which are almost completely co-precipitated by the beta-lipoproteins in the fluid being processed. For example, a given serum quantity should, in the most favorable case, be admixed with about 10 vol. % of a heparin buffer solution which contains 500–5,000 units per ml.

When mixing together volumetrically equal parts of whole serum or plasma and a phosphate-citrate buffer in which heparin is dissolved, at the resulting pH value of about 5.13, the precipitation of the complex occurs immediately and completely, and is specific. This means that only the beta-lipoproteins or low density lipoproteins are precipitated. The precipitated beta-lipoproteins can be separated from the supernatant fluid by, for example, a membrane filter of a pore size of up to 2 (preferably 0.4–0.8) micron or by simple centrifugation in a continuous flow process.

The process according to the invention is suitable both for therapy and for diagnostic tests.

In therapy, for example, plasma containing beta-lipoproteins can be separated from blood taken from a mammal, typically a human patient, and can be mixed according to the invention with a solution of heparin in a buffer. The beta-lipoproteins are thereby precipitated as a heparin-beta-lipoprotein complex at a pH value of 5.05 to 5.25, more particularly 5.13. The remaining serum (i.e., the remaining supernatant fluid) can be separated from the precipitate by filtration and thereafter returned to the bloodstream of the mammal.

For diagnostic purposes, the serum residue (supernatant fluid) separated from beta-lipoproteins, and/or the precipitated complex of beta-lipoproteins and heparin, can be subjected to further tests.

The specificity of the method according to the invention was checked both by quantitative immunological techniques and ultracentrifugation as well as by quantitative lipoprotein electrophoresis. The specific pH precipitation of low density lipoproteins described herein leads to a complete precipitation of this beta-lipoprotein class. The remaining filtrate contains only the lipoproteins HDL and VLDL.

The specificity of the process of the invention as described above and the use exclusively of physiological substances permits, firstly, an application on the extracorporeal circulation of patients suffering from hyper- or dyslipoproteinemia, and secondly, the selective elimination of LDL from the plasma in vitro makes it possible to determine this fraction either by calculation from the total cholesterol and the remaining filtrate, or by direct cholesterol determination on the precipitate, or by measuring the turbidity of the resulting precipitate. This direct determination of the LDL or beta-cholesterol is new and has not been described before in any competing method. The same applies to the selective elimination of LDL from whole plasma for therapeutic purposes.

Such process has been compared both with the preparative ultracentrifuge and with quantitative lipoprotein electrophoresis and, with both methods, has given correlation coefficients of over 0.98 in a series of over 100 patient sera. The specificity of the process is clearly superior to the ultracentrifuge. Compared with electrophoresis, the process of the invention has the advantage of the possibility of direct cholesterol determination of the beta-lipoproteins. The process can readily be conducted both in an automatic batch process and in a continuous-flow apparatus. The precision within the series as well as from day to day is under 2%.

THE APPARATUS

It is a further object of the invention to provide an apparatus for the extracorporeal precipitation of blood constituents, which apparatus is adapted to operate continuously in the operative phase without any complicated regulation of the quantities of fluids flowing in the system, to burden the patient as little as possible, and to avoid complicated and hence trouble-prone control systems.

The apparatus comprises a mixing means, such as a container, to which a patient's blood or blood components such as plasma is supplied via a first pump, and has a filter following down-stream from the container. The filtrate outlet of the filter is connected to a line leading back to the patient.

To accomplish the desired purposes according to the invention, the filter has a second outlet for the precipitate, which outlet is connected to a return line leading back into the container; the container is connected via a second pump with the outlet of a first reservoir containing a treatment agent, and the filtrate outlet of the filter is connected to a third pump whose output, during the normal extractive mode of operation, corresponds essentially to the sum of the outputs of the first and second pumps.

The container together with the filter and the return line form a closed cycle in which liquid circulates. Into this cycle an external liquid is introduced, via the first pump which pumps blood or blood constituents into the container and via the second pump which pumps the treatment agent, in the present instance, heparin in a buffer, into the container. From this closed cycle, liquid is withdrawn by the third pump from the filtrate outlet of the filter. Due to the fact that the output of the third pump is adapted to be the sum of the outputs of the first and second pumps, the liquid equilibrium in the cycle is essentially maintained, so that the liquid level in the container always remains approximately constant. Therefore, frequent switching on and off of the first pump is not necessary, and blood can be drawn from the patient at an even rate. It should be noted that the three named pumps are volumetric pumps whose output volume is proportional to their driving speed. To prevent contamination of the liquid to be pumped, preferably hose pumps are employed.

The output of the first pump is determined mainly by the reaction of the patient's body, because the apparatus must not withdraw too much blood from the patient, or withdraw blood too rapidly. For this reason, the system is desirably arranged so that the output of the first pump can be varied without upsetting the equilibrium of the circulation system. To this end, an advantageous development of the invention provides that the output of the first pump can be varied as a function of the conditions of blood removal from the patient, and that the drives of the first, second and third pumps are coupled together in such a way that the ratios of the three outputs remain constant during the normal extractive mode of operation.

Of advantage in this connection is the fact that the system can be operated with pump output quantities varying in time without the liquid equilibrium being lost. The first, second and third pumps are coupled together via their drives either mechanically or electrically, the first pump taking the lead and the speeds of the other two pumps automatically adapting themselves accordingly during the normal extractive mode of operation.

Despite the mutual matching of the outputs of the three pumps, it may happen that upon prolonged operation of the apparatus, the liquid level in the container rises increasingly. To limit such rising, the container comprises at least one level detector which, upon sensing that the level of fluid has risen to a predetermined level, is adapted to adjust the first pump to a lower output or to turn it off.

On the other hand, to avoid a drop of the liquid level in the container below a second predetermined level, the level detector means can be adapted to reduce the output of the third pump, or to turn it off, when such lower level is reached. These measures of limitation of the fluid level in the container to the range between the predetermined lower and upper values have the purpose of limiting the influence of constantly accumulative deviations in the liquid equilibrium of the cycle.

Inasmuch as the filter tends to become clogged after a period of use, an advantageous feature of the invention provides a flushing mode of operation. In converting to the flushing mode, the first and second pumps are turned off, while the third pump continues to operate. The apparatus further comprises a device which measures the flow resistance of the filter. This is done by sensing the difference in fluid pressure across the filter. In response to sensing a first predetermined pressure differential, the apparatus is adapted to close a valve in the line from the first reservoir, to open a valve in the line from a second reservoir containing a flushing solvent, to resume operation of the second pump, thereby pumping flushing solvent from the second reservoir into the container, and concurrently to operate appropriate valve means to establish a connection between the filtrate outlet (of the filter) and a drain. In this way, the liquid circulation behind the filter is interrupted or shut off and both the container and the filter are traversed by the flushing solvent, which thereafter is sent to the drain together with the filter residues.

The apparatus adapted for the therapeutic extracorporeal precipitation of blood components of whole serum, plasma or blood withdrawn directly from a mammal, typically a human patient, comprises
- mixing means having a first inlet, a second inlet, a third inlet, and an outlet;
- a first pump, the inlet of which is connected directly or indirectly, to a source of whole serum, plasma or blood from a mammal patient, and the outlet of which is connected to said mixing means via said first inlet thereof;
- a lipoprotein-complex filter having an inlet, a filtrate outlet and a precipitate outlet, said inlet being adapted to receive fluid from an outlet of said mixing means, and said precipitate outlet being connected to said third inlet of said mixing means;
- a first reservoir adapted to contain a treating agent and having an outlet;
- a second pump having an inlet which is connected by a conduit to an outlet of said first reservoir, and an outlet which is connected to said second inlet of said mixing means;
- a third pump having an inlet which is connected to said filtrate outlet of said filter, and having an outlet, and a conduit from said outlet connected to return means adapted for returning fluid to said mammal; and
- each of said pumps being volumetric pumps adapted to pump blood or fluid blood components, each of said pumps having drive means, and said drive means being adapted to maintain, during the normal extractive mode of operation of said apparatus, the volumetric output of fluid from said third pump corresponding essentially to the sum of the volumetric outputs from said first and second pumps.

Preferably, the rate of output of fluid from the first pump is variable as a function of the condition of the blood or fluid blood components withdrawn from said patient, and the individual means driving each of the first, second and third pumps are adapted to be coupled together to maintain, during the normal extractive mode of operation, a constant volumetric ratio of fluid being pumped by said first, second and third pumps.

The apparatus preferably additionally comprises at least one fluid level detector means associated with the mixing means which is adapted to sense the level of fluid in such mixing means, and level control actuating means which is responsive to the sensing of such level of fluid and which is adapted to reduce or increase the amount of fluid pumped by the first pump or by the third pump in response to sensing a fluid level above or below a first predetermined level. This may be accomplished by, for instance, having the actuating means adapted to reduce or terminate the fluid delivered by the first pump, in order to reduce the fluid level in the mixing means, or adapted to reduce or terminate the fluid delivered by the third pump, in order to increase the fluid level in the mixing means.

For purposes of conducting a flushing mode of operation, whereby the filter is flushed of accumulated lipoprotein-heparin complex, the apparatus additionally comprises a first valve means in the conduit connecting the first reservoir to the inlet of the second pump; a second reservoir adapted to contain a flushing solvent and having an outlet connected by second valve means to the inlet of the second pump; and the conduit from the outlet of the third pump comprising a branched line, one branch comprising a third valve means (which also comprises parts of the return means), and the second branch comprising a fourth valve means and being adapted to discharge fluid from the apparatus system, e.g., into a container or to a drain.

The apparatus also advantageously comprises pressure differential sensing means adapted to sense the pressure differential across the lipoprotein-complex filter and being adapted, in response to sensing a first predetermined pressure differential, to close the first valve means and to open the second valve means to permit fluid to be withdrawn from the second reservoir (rather than the first reservoir), to resume operation of the second pump, and to close the third valve means and to open the fourth valve means in the branches of the conduit leading from the third pump.

The apparatus can be adapted for transition from a flushing mode of operation to an extractive mode of operation by having the pressure differential sensing means be further adapted, in response to sensing a second predetermined pressure across the filter, to terminate the flow of solvent from the second reservoir while continuing to operate the third pump. The third pump continues to operate until the contents of the container and of the cycle have been discharged from the apparatus system. Thereafter, a new cycle for the extractive mode of operation may be started.

In the following, an embodiment of the apparatus of the invention for the performance of a plasmapheresis with precipitation of the low density lipoproteins is explained more specifically with reference to the drawings.

Figure 2:
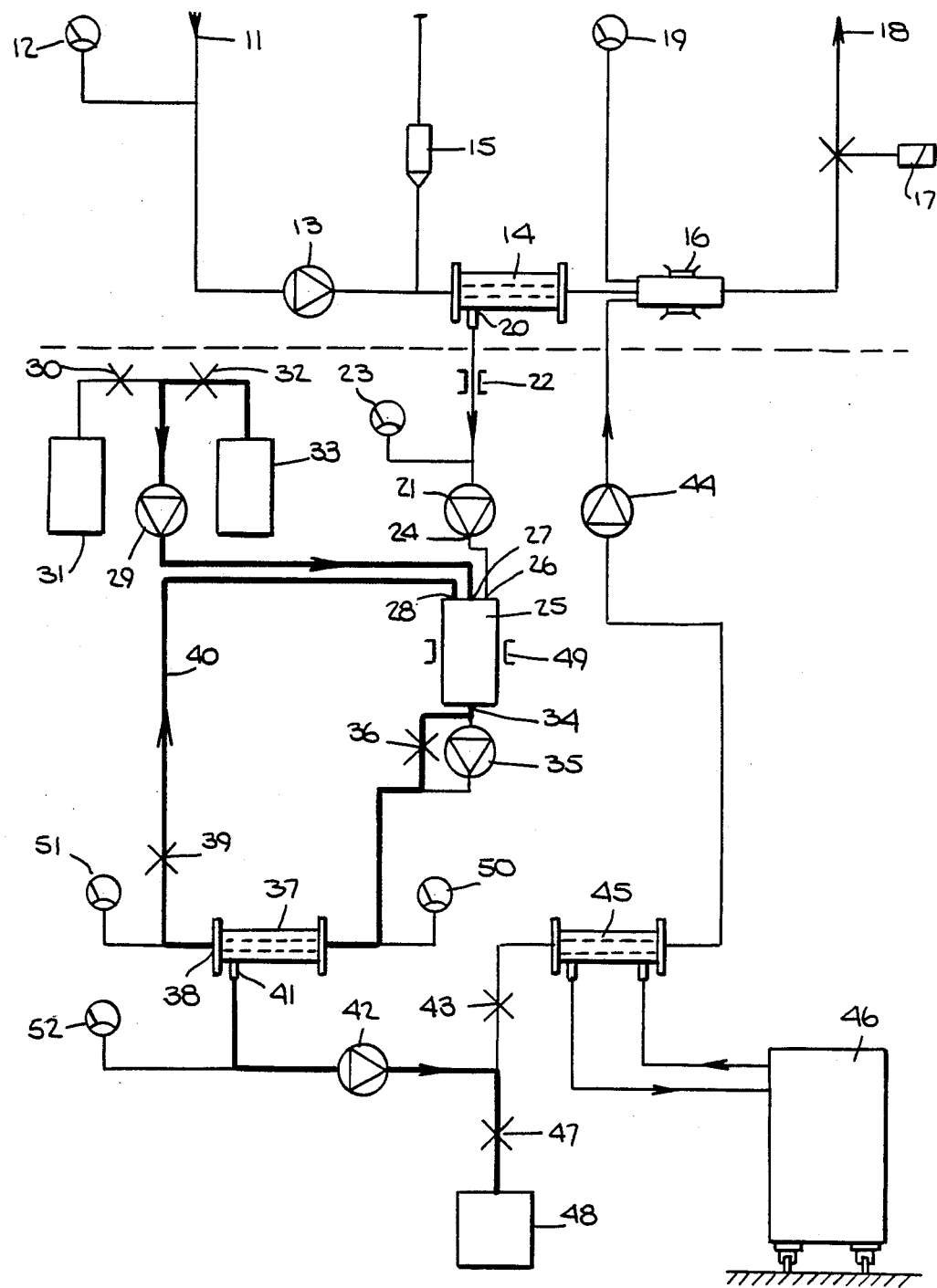

FIG. 1 shows a schematic representation of the system, where the lines which in the extractive mode of operation carry a flow are drawn in bolder lines; and FIG. 2 shows the system of FIG. 1, but where the lines which carry flow during the flushing mode of operation are drawn in bolder lines.

Referring now to FIGS. 1 and 2, a system, already known in the prior art, for withdrawing blood from a patient, and returning it after it has been processed, is depicted above the dashed horizontal line of the drawings. Via a patient connection 11, blood is drawn from the patient under constant monitoring by a pressure gauge 12. This blood is sent via a pump 13 to a plasma filter 14, anticoagulant optionally having been admixed from a vessel 15. From filter 14, the blood reduced by a certain quantity of plasma flows through an air trap 16 and a solenoid valve 17 to the return connection 18 of the patient. The return pressure is monitored by a pressure measuring device 19. The blood plasma withdrawn from the patient leaves filter 14 through the latter's filtrate outlet 20. Filter 14 is, for example, a capillary filter traversed by the blood, with the finer blood components escaping laterally through the membrane walls while the coarser blood components move on to the air trap 16.

By means of first pump 21, a preselectable quantity of blood plasma is drawn from plasma filter 14. First pump 21 is, as are the second, third, and fourth pumps referred to herein, a hose pump, or a peristaltic pump which is self-priming and volumetrically conveys a quantity of plasma proportional to the driving speed. Between plasma filter 14 and first pump 21 is an optional blood leakage detector 22 as well as pressure gauge 23. Outlet 24 of first pump 21 is connected to a mixing means here depicted as container 25 by means of first inlet 26. Container 25 also has a second inlet 27 and a third inlet 28. The inlets are desirably located at the upper end of container 25.

Second inlet 27 of container 25 is connected to the outlet of second pump 29, the inlet of which is connectable via a first valve means comprising valve 30 with a first reservoir 31 adapted to contain a treating agent such as an acetate buffer solution with heparin. The inlet of second pump 29 is also connectable via a second valve means 32 to second reservoir 33 adapted to contain a flushing solvent.

Outlet 34 of container 25 is connected to recirculation pump 35, which is optionally connected in parallel by means of valve 36. The outlet of recirculation pump 35 is connected to the inlet of filter 37, the precipitate outlet 38 of which is connected via a valve 39 and a return line 40 to inlet 28 of container 25. Pump 35 has an output which exceeds the output of third pump 42 by an amount at least sufficient to furnish an adequate amount of recirculating fluid in return line 40.

Filtrate outlet 41 of filter 37 is connected to third pump 42, the outlet of which is connected to return means adapted for returning fluid to the patient. Such return means as here depicted comprises a third valve means comprising valve 43, and fourth pump 44. It also includes dialyzer 45 which on the flush solution side is traversed by a dialysis flush solution from dialysis equipment 46. In dialyzer 45, the buffer component of the treating agent, and the remaining active ingredient, such as heparin, from reservoir 31 are eliminated. Thereafter, the plasma flows via fourth pump 44 to air trap 16 and thus to the extracorporeal blood circulation. Fourth pump 44 runs at the same speed as first pump 21, so as to maintain the liquid balance of the patient to be treated. Through the dialyzing flushing liquid from the dialysis equipment 46, there occurs in filter 45 at the same time a rise of the pH value and of the temperature of the returning plasma to body values. Optionally, instead of the dialysis equipment, a liquid may be supplied to the dialyzer 45 via an open cycle.

A second branch of the conduit from the outlet of third pump 42 comprises fourth valve means 47, and discharges into a waste container or drain 48.

Fluid level detector means 49 is adapted to sense the level of the fluid in container 25. Detector means 49 also comprises level control actuating means, the operation of which is described hereinafter.

Pressure gauges 50 and 51 monitor the fluid pressure at, respectively, the inlet of filter 37 and the precipitate outlet 38 thereof. Gauge 52 may optionally be provided to measure the fluid pressure at filtrate outlet 41.

A pressure differential sensing means is adapted to sense the pressure differential between the inlet of filter 37 and its outlet 38, and is adapted to operate (to open or close) certain valve means, and to operate certain pumps, in response to sensing certain predetermined pressure differentials across filter 37. Such sensing means comprises a pressure differential detector 53, and associated signal-transmitting means connected to the pressure gauges 50 and 51, and to the various valve means (typically electrical wiring, and here depicted as dashed lines) and also the various pump driving means.

The normal extractive mode of operation of the apparatus is the on-stream therapeutic processing of blood or blood components from a patient with the fluid level in container 25 at a preselected level. Blood plasma is pumped by first pump 21 into container 25, while simultaneously a treating solution, such as an acetate buffer solution with heparin, is supplied through second pump 29 via the open valve 30. In commencing this operation, third pump 42 is at first turned off. After the desired fluid level has been reached in container 25, the level detector 49 responds and turns third pump 42 on. Pump 42 then runs at a speed which corresponds to the sum of the speeds of first pump 21 and second pump 29. Third pump 42 thus conveys plasma out of filter 37, while the precipitate is retained in filter 37 because of the chosen pore size. Pump 35, which maintains the liquid circulation in the cycle, has a relatively high output, so that the precipitate containing the low density lipoproteins is flushed back into container 25 via return line 40. Fourth pump 44 runs at the same speed as first pump 21. The ratio of the speeds of second pump 29 and first pump 21 is held constant. The plasma filtrate from the low density lipoproteins is supplied to dialyzer 45 via third pump 42 and the open valve 43. In this mode of operation, valves 32 and 47 are closed.

As the proportion of precipitate in container 25 and in filter 37 increases continuously, it is necessary at certain intervals to remove the precipitate from container 25 and from the recirculation cycle. This is done in the flushing mode of operation. First, the plasma inflow via first pump 21 and the inflow of treating composition via second pump 29 is stopped by stopping these pumps. Also, pump 35 is stopped, and bypass valve 36 is opened. (It is also possible to let pump 35 continue to run, in which situation bypass valve 36 is unnecessary.) Third pump 42 continues to withdraw through filter 37 plasma which has been freed from low density lipoproteins and pumps this plasma through the dialysis apparatus to fourth pump 44. When container 25 has run empty, the pressure difference increases between the inlet of filter 37 and outlet 38. This increase in pressure difference is ascertained by pressure differential detector 53, which senses the differences between the signals of gauges 50 and 51. After the pressure difference has exceeded a first predetermined amount, second pump 29 is started, valve 47 is opened and valve 43 is closed. In addition, valve 30 is closed and valve 32 is opened. Now flushing solvent flows from reservoir 33 to container 25. Valve 39 opens and recirculation pump 35 starts. By reason of the recirculation of the solvent, the precipitate which has remained in the lines and in filter 37 is dissolved. After the working level of fluid has been reached in container 25, third pump 42 starts up and pumps the solvent with the dissolved precipitate via the open valve 47 into the container 48. When sufficient precipitate has been dissolved, a lower pressure of a second predetermined value is sensed by the pressure differential detector 53. Thereupon, second pump 29 is turned off and valve 32 closed. Alternatively, the same process also can be actuated by the pressure gauge 52 indicating a relatively low vacuum of predetermined value. Third pump 42 continues to run until the contents of container 25 and of the apparatus between container 25 and pump 42 have been pumped into container 48. Thereafter, a new cycle for precipitation of low density lipoproteins is started.

It should be understood that the third and fourth valve means (valves 43 and 47, respectively) may be combined into a single device if desired. Also, the first and second valve means (valves 30 and 32) may be combined into a single device, which may include an intermediate position preventing flow from either reservoir.

During the extractive mode of operation, the lines which carry a flow are from patient connection 11, through pump 13, filter 14, air trap 16 and back to return connection 18. From outlet 20 of filter 14, fluid flows through first pump 21 to container 25, and from first reservoir 31 through valve 30 and second pump 29 to container 25. From container 25, the flow is through recirculation pump 35 into filter 37, from filter 37 via outlet 37 to third pump 42, valve 43, dialyzer 45, and fourth pump 44 back to air trap 16. In addition, fluid flows from outlet 38 through valve 39 and return line 40 to inlet 28 of container 25.

During the flushing mode of operation, fluid flows from second reservoir 33 via valve 32 through second pump 29 to container 25. From thence, fluid flows through pump 35 to filter 37, and from thence through outlet 41 via third pump 42 and valve 47 to drain 48. In addition, fluid flows from outlet 38 through valve 39 and return line 40 to inlet 28 of container 25.

The invention as described above will be further explained in the following examples.

EXAMPLE 1

Plasma is mixed with an equal quantity of a citrate, phosphate or acetate buffer (0.05 M, pH 4.15). After adding a quantity of heparin (5000 U/ml) which constitutes one tenth of the plasma quantity used, there forms a yellow-white precipitate which consists of the precipitated beta-lipoproteins and mainly fibrogen.

EXAMPLE 2

One hundred microliters of serum are mixed with 1 ml of a solution having the following composition: 0.0641 M sodium citrate, pH 5.04, 1% Liqemin 25 000 (Roche). The mixture is centrifuged for 10 minutes in an Eppendorf centrifuge. The cholesterol content of the supernatant fluid corresponds to the cholesterol content of the VLDL and HDL. The LDL have been precipitated and can be calculated from the difference between the whole serum cholesterol minus VLDL+HDL cholesterol.

THE USE OF POLYANIONS

It also has been discovered that for diagnostic purposes all other polyanions usable for lipoprotein precipitation in connection with the use of bivalent cations are suitable. Particularly suitable polyanions include dextran sulfate of the molecular (weight) range 10,000 to 2,000,000, as well as sodium-phosphorus tungstate.

Accordingly, a further embodiment of the invention relates to a process for the selective extracorporeal precipitation of low density lipoproteins or beta-lipoproteins from whole serum or plasma for diagnostic purposes, which process comprises mixing whole serum or blood plasma and a composition comprising polyanions in an aqueous buffer solution, whereby a complex of beta-lipoproteins and polyanions is precipitated at the isoelectric point at a pH in the range of from about 5.05 to about 5.25, and typically thereafter such complex is separated from the remaining supernatant fluid, and the precipitate and/or the filtrate is available for further analysis.

In this embodiment of the process of the invention, more particularly, the complex of a polyanion, e.g., dextran sulfate or sodium-phosphorus tungstate, and beta-lipoproteins is precipitated at a pH value of 5.13.

The polyanion, such as dextran sulfate, is dissolved in a buffer and mixed with the whole serum or plasma. The buffer serves to adjust and stabilize the stated pH values. All buffer mixtures which assure stability in the stated pH range are in principle usable in practicing the process. Suitable buffers have proven to be a phosphate buffer, a phosphate-citrate buffer, a lactate buffer, or an acetate buffer, or mixtures thereof.

The ratio of buffer to serum or plasma or blood volume may be between 1:5 and 1000:1 by volume. A ratio between 2:1 and 10:1 buffer to serum was found to be most favorable for the selective elimination of the low density lipoproteins from the blood for diagnostic purposes.

The polyanion concentration is not a particularly critical variable. It is desirable, however, to employ polyanion concentrations which are almost completely co-precipitated by the beta-lipoproteins in the fluid being processed. For example, a given serum quantity should, in the most faborable case, be admixed with 10 vol. % of a 6% dextran-sulfate buffer solution or, respectively, a 40% sodium-phosphorus tungstate buffer solution.

When mixing together volumetrically equal parts of the whole serum or plasma and a phosphate-citrate buffer in which the polyanion is dissolved, at the resulting pH value of about 5.13, the precipitation occurs immediately and completely and is specific. This means that only the beta-lipoproteins or low density lipoproteins are precipitated. The precipitated beta-lipoproteins can be separated from the remaining serum by, for example, a membrane filter of a pore size of about 0.2 to 2 micron or by simple centrifugation in a continuous flow process.

This embodiment of the process of the invention is suitable for diagnostic tests.

In diagnostic testing, both the serum residue freed from beta-lipoproteins and the precipitated complex of beta-lipoproteins and polyanion can be subjected to further tests.

The specificity of this embodiment was checked both by quantitative immunological techniques and by ultracentrifugation as well as by quantitative lipoprotein electrophoresis. The specific pH precipitation of low density lipoproteins here described leads to a complete precipitation of this beta-lipoprotein class. The remaining filtrate contains only the lipoproteins HDL and VLDL.

The selective elimination of LDL from the plasma in vitro makes it possible to determine this fraction either by difference calculation from the total cholesterol and the remaining filtrate, or by direct cholesterol determination in the precipitate, or respectively by turbidity measurement of the resulting precipitate. This direct determination of the LDL or beta-cholesterol is new and has not been described before in a competing method.

This form of the process has been compared both with the preparative ultracentrifuge and with quantitative lipoprotein electrophoresis and, with both methods, has given correlation coefficients of over 0.98 in a series of over 100 patient sera. The specificity of the process is clearly superior to the ultracentrifuge. As compared with electrophoresis, the process has the advantage of the possibility of direct cholesterol determination of the beta-lipoproteins. The process can readily be conducted both in an automatic batch process and in a continuous-flow apparatus as a mechanized method. The precision within the series as well as from day to day is under 2%.

The embodiment of the invention is further explained in the following examples.

EXAMPLE 3

Plasma is mixed with an equal quantity of a citrate, phosphate, or acetate buffer (0.05 M, pH 4.15). After adding about 10 vol. % of a 6% dextran sulfate buffer solution, there forms a yellow-white precipitate which consists of the precipitated beta-lipoproteins and mainly fibrinogen.

EXAMPLE 4

One hundred microliters of serum are mixed with 1 ml of a solution having the following composition: 0.0641 M sodium citrate (pH 5.04), 1 vol. % of a 40% sodium-phosphorus tungstate buffer solution. The mixture is centrifuged for 10 minutes in an Eppendorf centrifuge. The cholesterol content of the supernatant fluid correspond to the cholesterol content of VLDL and HDL. The LDL been precipitated and can be calculated from the difference between the whole serum cholesterol minus (VLDL plus HDL cholesterol).

While the processes and apparatus described herein constitute preferred embodiments of the invention, it is to be understood that there are variations in materials and equipment which may be employed which are included in the invention as defined by the appended claims. Therefore, the detailed description should be considered illustrative rather than as restrictive.

Having thus described the invention, we claim:

1. A therapeutic process for the selective extracorporeal precipitation of beta-lipoproteins from blood, plasma, serum and solutions thereof, which process comprises withdrawing blood from a mammal, mixing said blood, plasma or serum obtained therefrom, or solutions thereof, with a physiologically non-toxic composition comprising a buffer and an effective amount of a low density lipoprotein precipitating substance selected from the group consisting of heparin and dextran sulfate, whereby a complex of beta lipoprotein-precipitating substance is selectively precipitated, in preference to precipitating pre-beta-lipoproteins or chylomicrons, substantially at the isoelectric point of the complex at a pH in the range of from about 5.05 to about 5.25, separating said complex from at least a portion of the remaining supernatant fluid, and returning to said mammal at least a portion of the supernatant fluid from which said complex has been separated.

2. The process of claim 1, wherein the precipitation of said complex is effected at a pH of 5.13.

3. The process of claim 1, wherein said buffer is selected from the group consisting of a phosphate buffer, a citrate buffer, a lactate buffer, and an acetate buffer, and mixtures thereof.

4. The process of claim 1, wherein the ratio of the buffer to any of said blood, plasma or serum is in the range of from about 1:5 to about 5:1, by volume.

5. The process of claim 4, wherein said volumetric ratio is about 1:1.

6. The process of claim 1, wherein the concentration of heparin is approximately equal to the concentration of beta-lipoproteins.

7. A diagnostic process for the selective extracorporeal precipitation of beta-lipoproteins from blood, plasma, serum, or a solution thereof, which process comprises mixing blood, plasma, serum or a solution thereof and a composition comprising a buffer and heparin, whereby a complex of beta-lipoprotein-heparin is selectively precipitated, in preference to precipitating pre-beta-lipoproteins or chylomicrons, substantially at the isoelectric point of the complex at a pH in the range of from about 5.05 to about 5.25, separating said complex from at least a portion of the remaining supernatant fluid, and analyzing at least a portion of said complex or of the supernatant fluid from which said complex has been separated.

8. The process of claim 7, wherein the precipitation of said complex is effected at a pH of 5.13.

9. The process of claim 7, wherein said buffer is selected from the group consisting of a phosphate buffer, a citrate buffer, a lactate buffer, and an acetate buffer, and mixtures thereof.

10. The process of claim 8, wherein the ratio of the buffer to any of said blood, plasma or serum is in the range of from about 2:1 to about 10:1, by volume.

11. The process of claim 7, wherein the concentration of heparin is approximately equal to the concentration of beta-lipoproteins.

12. A diagnostic process for the selective extracorporeal precipitation and determination of beta-lipoproteins from blood, plasma, serum or a solution thereof, which process comprises mixing blood, plasma, serum or a solution thereof and a composition comprising a buffer and dextran sulfate, whereby a complex of beta-lipoprotein-dextran sulfate is selectively precipitated, in preference to precipitating pre-beta-lipoproteins or chylomicrons, substantially at the isoelectric point at a pH in the range of from about 5.05 to about 5.25, separating said complex from at least a portion of the remaining supernatant fluid, and analyzing at least a portion of said complex or of the supernatant fluid from which said complex has been separated.

13. A diagnostic process for the selective extracorporeal precipitation and determination of beta-lipoproteins from blood, plasma or serum, which process comprises mixing blood, plasma or serum and a composition consisting essentially of a buffer and a polyanion precipitating agent, whereby a complex of beta-lipoprotein-polyanion is selectively precipitated, in preference to precipitating pre-beta-lipoproteins or chylomicrons, substantially at the isoelectric point at a pH in the range of from about 5.05 to about 5.25, separating said complex from at least a portion of the remaining supernatant fluid, and analyzing at least a portion of said complex or of the supernatant fluid from which said complex has been separated.

14. The process of claim 13, wherein said polyanions are dextran sulfate having a molecular weight in the range of from about 10,000 to about 2,000,000, or sodium-phosphorous tungstate.

15. The process of claim 13, wherein the precipitation of said complex is effected at a pH of 5.13.

16. The process of claim 13, wherein said buffer is selected from the class consisting of a phosphate buffer, a citrate buffer, a lactate buffer, and an acetate buffer, and mixtures thereof.

17. The process of claim 13, wherein the ratio of the buffer to any of said blood, plasma or serum is in the range of from about 2.1 to about 10:1, by volume.

18. A process suitable for the therapeutic and diagnostically substantially selective precipitation of low density lipoproteins which comprises administering to a volume of blood, plasma, serum or a solution of blood or plasma a therapeutically or diagnostically effective amount of a low-density lipoprotein precipitating substance selected from the group consisting of heparin and dextran sulfate and a buffer solution selected from the group consisting of a phosphate buffer, a citrate buffer, a lactate buffer, an acetate buffer and mixtures thereof, at a pH in the range of about 5.05 to 5.25, whereby a complex of low density lipoprotein and precipitating substance is selectively precipitated.

* * * * *